(12) United States Patent
Vogt et al.

(10) Patent No.: US 11,959,227 B2
(45) Date of Patent: *Apr. 16, 2024

(54) CREPED MULTI-PLY TISSUE PRODUCT

(71) Applicant: Kimberly-Clark Worldwide, Inc., Neenah, WI (US)

(72) Inventors: Kevin Joseph Vogt, Neenah, WI (US); Mark William Sachs, Appleton, WI (US); Erin Ann McCormick, Neenah, WI (US); Devon Gaynelle Curley, Menasha, WI (US); Sara Jane Wille Stabelfeldt, Appleton, WI (US); Nathan John Vogel, Neenah, WI (US); Christopher Steven LeCount, Greenville, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/129,280

(22) Filed: Mar. 31, 2023

(65) Prior Publication Data
US 2023/0235513 A1    Jul. 27, 2023

Related U.S. Application Data

(63) Continuation of application No. 17/869,455, filed on Jul. 20, 2022, now Pat. No. 11,649,591, which is a continuation of application No. 17/425,377, filed as application No. PCT/US2020/025236 on Mar. 27, 2020, now Pat. No. 11,427,968.

(60) Provisional application No. 62/825,903, filed on Mar. 29, 2019.

(51) Int. Cl.
| | |
|---|---|
| D21H 27/30 | (2006.01) |
| A47K 10/16 | (2006.01) |
| B31F 1/07 | (2006.01) |
| B31F 1/12 | (2006.01) |
| D21H 17/24 | (2006.01) |
| D21H 17/36 | (2006.01) |
| D21H 19/10 | (2006.01) |
| D21H 19/12 | (2006.01) |
| D21H 21/06 | (2006.01) |
| D21H 21/24 | (2006.01) |
| D21H 27/00 | (2006.01) |
| D21H 27/02 | (2006.01) |
| D21H 27/40 | (2006.01) |

(52) U.S. Cl.
CPC ........... D21H 27/005 (2013.01); A47K 10/16 (2013.01); D21H 17/24 (2013.01); D21H 17/36 (2013.01); D21H 19/12 (2013.01); D21H 21/06 (2013.01); D21H 21/24 (2013.01); D21H 27/02 (2013.01); D21H 27/40 (2013.01); B31F 1/07 (2013.01); B31F 1/12 (2013.01); B31F 2201/0764 (2013.01)

(58) Field of Classification Search
CPC ...... D21H 27/005; D21H 17/24; D21H 27/02; D21H 27/27; D21H 27/30; D21H 17/36; D21H 19/12; D21H 21/06; D21H 21/24; D21H 27/002; D21H 27/40; B31F 1/07; B31F 1/12; B31F 2201/0764; B31F 1/126; B31F 1/14; B31F 2201/0761; A61K 8/0208; A61K 8/81; A47K 10/16

See application file for complete search history.

(56) References Cited

U.S. PATENT DOCUMENTS

| | | | |
|---|---|---|---|
| 4,063,995 | A | 12/1977 | Grossman |
| 4,886,579 | A | 12/1989 | Clark et al. |
| 8,282,776 | B2 | 10/2012 | Smith et al. |
| 9,121,137 | B2 | 9/2015 | Viazmensky et al. |
| 9,951,477 | B2 | 4/2018 | Zwick et al. |
| 10,132,041 | B2 | 11/2018 | Hermans et al. |
| 10,145,069 | B2 | 12/2018 | Shannon et al. |
| 10,337,148 | B2 | 7/2019 | Rouse et al. |
| 10,337,149 | B2 | 7/2019 | Rouse et al. |
| 10,385,516 | B2 | 8/2019 | Zawadzki et al. |
| 10,428,465 | B2 | 10/2019 | Rouse et al. |
| 10,487,452 | B1 | 11/2019 | Qin et al. |
| 10,550,522 | B2 | 2/2020 | Shannon et al. |
| 10,753,046 | B2 | 8/2020 | Zawadzki et al. |
| 10,947,673 | B2 | 3/2021 | Rouse et al. |
| 11,053,643 | B2 | 7/2021 | Rouse et al. |
| 11,371,191 | B2 | 6/2022 | Vogt et al. |
| 11,427,968 | B2 * | 8/2022 | Vogt ................. D21H 27/30 |
| 11,566,379 | B2 * | 1/2023 | Rouse ............... D21H 27/002 |
| 11,649,591 | B2 * | 5/2023 | Vogt ................. D21H 27/005 162/123 |
| 11,773,538 | B2 * | 10/2023 | Vogt ................. D21H 27/002 162/109 |
| 11,795,626 | B2 * | 10/2023 | Vogt ................. B31F 1/126 |
| 2007/0144697 | A1 | 6/2007 | Dyer et al. |
| 2008/0073045 | A1 | 3/2008 | Dyer et al. |
| 2014/0050890 | A1 | 2/2014 | Zwick et al. |
| 2014/0178660 | A1 | 6/2014 | Kim et al. |
| 2016/0097163 | A1 | 4/2016 | Rekoske et al. |
| 2016/0145809 | A1 | 5/2016 | Hermans et al. |
| 2018/0016749 | A1 | 1/2018 | Zawadzki et al. |
| 2018/0142419 | A1 | 5/2018 | Rouse et al. |
| 2018/0142421 | A1 | 5/2018 | Rouse et al. |

(Continued)

FOREIGN PATENT DOCUMENTS

| | | |
|---|---|---|
| KR | 101794487 B1 | 11/2017 |
| WO | 2005113895 A1 | 12/2005 |

(Continued)

*Primary Examiner* — Jose A Fortuna

(74) *Attorney, Agent, or Firm* — KIMBERLY-CLARK WORLDWIDE, INC.

(57) ABSTRACT

The creped multi-ply tissue products are durable, smooth and have low levels of Slough. In certain instances, the creped multi-ply tissue products are produced using a creping composition comprising a non-crosslinked latex polymer. The creped multi-ply tissue products may have a geometric mean tensile (GMT) from about 700 to about 1,500 g/3", a basis weight from about 45 to about 60 gsm and a Slough less than about 2.00 mg, such as from about 0.10 to about 2.00 mg. The inventive tissue products also have good durability, such as a Durability Index from about 10.0 to about 20.0, smooth surfaces, such as a TS750 value from about 15.0 to 40.0 and low stiffness, such as a Stiffness Index less than about 10.0.

13 Claims, 7 Drawing Sheets

(56) References Cited

U.S. PATENT DOCUMENTS

| | | |
|---|---|---|
| 2019/0309482 A1 | 10/2019 | Zawadzki et al. |
| 2020/0032456 A1 | 1/2020 | Paulson et al. |
| 2020/0035456 A1 | 1/2020 | Fan et al. |
| 2020/0102705 A1 | 4/2020 | Rouse et al. |
| 2020/0115853 A1 | 4/2020 | Shannon et al. |
| 2021/0156093 A1 | 5/2021 | Rouse et al. |
| 2021/0238806 A1 | 8/2021 | Tirimacco |
| 2021/0277603 A1 | 9/2021 | Anderson et al. |
| 2021/0285159 A1 | 9/2021 | Burazin et al. |
| 2021/0292973 A1 | 9/2021 | Rouse et al. |
| 2022/0042248 A1 | 2/2022 | Vogt et al. |
| 2022/0090321 A1 | 3/2022 | Weisman et al. |
| 2022/0090324 A1* | 3/2022 | Vogt .................. D21H 27/40 |
| 2022/0178079 A1 | 6/2022 | Tirimacco et al. |
| 2022/0228322 A1 | 7/2022 | Vogt et al. |
| 2022/0282428 A1 | 9/2022 | Vogt et al. |
| 2022/0287924 A1 | 9/2022 | Monson et al. |
| 2022/0332085 A1 | 10/2022 | Monson et al. |
| 2022/0364310 A1* | 11/2022 | Vogt .................. D21H 27/30 |
| 2023/0143624 A1* | 5/2023 | Satori ................. B32B 3/266 162/123 |
| 2023/0148320 A1* | 5/2023 | Satori ................. D21H 27/02 162/111 |
| 2023/0235513 A1* | 7/2023 | Vogt .................. D21H 27/002 162/123 |
| 2024/0003093 A1* | 1/2024 | Vogt .................. D21H 21/146 |

FOREIGN PATENT DOCUMENTS

| | | |
|---|---|---|
| WO | 2020205524 A1 | 10/2020 |
| WO | 2020247205 A1 | 12/2020 |
| WO | 2021194504 A1 | 9/2021 |
| WO | 2021194505 A1 | 9/2021 |

* cited by examiner

CREPED MULTI-PLY TISSUE PRODUCT

RELATED APPLICATIONS

The present application is a continuation application and claims priority to U.S. patent application Ser. No. 17/869,455, filed Jul. 20, 2022, now U.S. Pat. No. 11,649,591, which is a continuation application and claims priority to U.S. patent application Ser. No. 17/425,377, filed on Jul. 23, 2021, now U.S. Pat. No. 11,427,968, which is a national-phase entry, under 35 U.S.C. § 371, of PCT Patent Application No. PCT/US20/25236, filed on Mar. 27, 2020, which claims benefit of U.S. Provisional Application No. 62/825,903, filed on Mar. 29, 2019, all of which are incorporated herein by reference.

BACKGROUND

Absorbent paper products such as paper towels, facial tissues and other similar products are designed to include several important properties. For example, the products should have good bulk, a soft feel and should be highly absorbent. The product should also have good strength even while wet and should resist tearing. Unfortunately, it is very difficult to produce a high strength paper product that is also soft and highly absorbent. Usually, when steps are taken to increase one property of the product, other characteristics of the product are adversely affected. For instance, softness is typically increased by decreasing or reducing fiber bonding within the paper product. Inhibiting or reducing fiber bonding, however, adversely affects the strength of the paper web.

One tissue manufacturing process for balancing often competing physical properties is disclosed in U.S. Pat. No. 7,462,258. The process, which may be adapted to print binder on one or both sides of the web and typically involves a single creping step. The binder material is a crosslinked latex and comprises an azetidinium-reactive polymer. The presence of an azetidinium-reactive polymer enables the binder to crosslink both with itself and cellulose of the fibrous web. In this manner, the crosslinked latex of the '258 patent forms covalent bonds with cellulose of the fibrous web. Thus, while the '258 discloses an improved process for producing tissue products having good bulk, softness and good absorbency, the resulting products comprise a binder that forms covalent bonds with cellulose of the fibrous web, impeding breaking apart of the web when wetted.

An alternate to the crosslinked latex binders of the '258 patent is disclosed in U.S. Pat. No. 9,121,137, which discloses crosslinked a latex binder comprising a primary polymer and a polyfunctional aldehyde. The polyfunctional aldehyde, like the azetidinium-reactive polymer of the '258 patent, enables the binder to form covalent bonds with cellulose of the fibrous web. As such, products produced according to the '137 patent retain a significant portion of their tensile strength after being wetted for an extended period.

Accordingly, there remains a need in the art for a tissue manufacturing process for balancing the often competing physical properties, such as bulk, hand-feel and absorbency, while also providing a product that is readily dispersible.

SUMMARY

The present invention provides creped tissue webs, and products produced therefrom, that are generally durable, flexible and have a smooth surface. The inventive products generally comprise two or more tissue webs that have been prepared by a creping process and more preferably by a print creping process. The print creping process may be adapted to dispose a non-crosslinked latex polymer on at least one of the outer surfaces of the tissue product to provide the product with improved durability. Surprisingly, however, the presence of the non-crosslinked latex polymer does not negatively affect the stiffness of the product such that the products generally have a Stiffness Index less than about 6.5.

In other instances, the tissue products of the present invention generally have low levels of Slough. Slough generally results from the release of loosely bound fibers from the surface of the tissue product in use and is often an issue when producing soft, low stiffness tissue products. The inventive tissue products surprisingly have both low Slough levels despite having good softness and low stiffness. For example, in one embodiment the present disclosure provides a creped tissue product, such as a multi-ply creped tissue product comprising two or more plies, having a non-cross linked latex polymer disposed on at least one of its outer surface, the product having a geometric mean tensile (GMT) from about 800 to about 1,700 g/3", a basis weight from about 45 to about 60 gsm and a Slough less than about 2.00 mg, more preferably less than about 1.50 mg, such as from about 0.10 to about 2.00, such as from about 0.25 to about 1.50 mg.

In other embodiments the invention provides a rolled tissue product comprising a spirally wound tissue web, the web having a geometric mean tensile strength (GMT) greater than about 700 g/3" and a Slough less than about 2.00 mg.

In another embodiment the present invention provides a rolled tissue product comprising a spirally wound embossed, multi-ply tissue web having a first outer surface comprising a plurality of embossments and a non-crosslinked latex polymer disposed thereon and a second outer surface comprising a and a non-crosslinked latex polymer disposed thereon, the product having a basis weight from about 45 to about 60 grams per square meter (gsm), a GMT from about 800 to about 1,700 g/3" and a Slough from about 0.10 to about 2.00 mg.

In other embodiments the present invention provides a creped, multi-ply tissue product comprising a first creped tissue ply and a second creped tissue ply, the product having a TS750 value less than about 35, such as from about 20 to about 30, and a Stiffness Index less than about 10.0, such as from about 4.0 to about 8.0. In this manner the present invention provides creped tissue products having a smooth surface and good flexibility. In certain instances, the products are also highly durable, such as having a Durability Index greater than about 10.0, such as from about 10.0 to about 20.0.

In yet other embodiments the present invention provides a creped, multi-ply tissue product comprising: (a) a first and a second creped tissue ply; (b) a creping composition consisting essentially of a non-crosslinked vinyl acetate-ethylene polymer and optionally an anti-blocking agent disposed on the first and the second tissue ply; (c) a softening composition selected from the group consisting of a polyhydroxy compound having a molecular weight of at least about 1,000 g/mol, a diamidoamine quaternary compound, an ester quaternary compound, an alkoxy alkyl quaternary compound, a benzyl quaternary compound, an alkyl quaternary compound, an imidazolinium quaternary compound, a polysiloxane, glycerin, and combinations thereof disposed on the first or the second tissue ply; and (d) a plurality of embossments disposed on the first or the second tissue ply; wherein the product has a GMT from about 800 to about 1,700 g/3", a Slough from about 0.25 to about 1.50 mg, and a TS750 value less than 40, such as from about 20 to about 40, such as from about 20 to about 30.

DEFINITIONS

Figure 1:
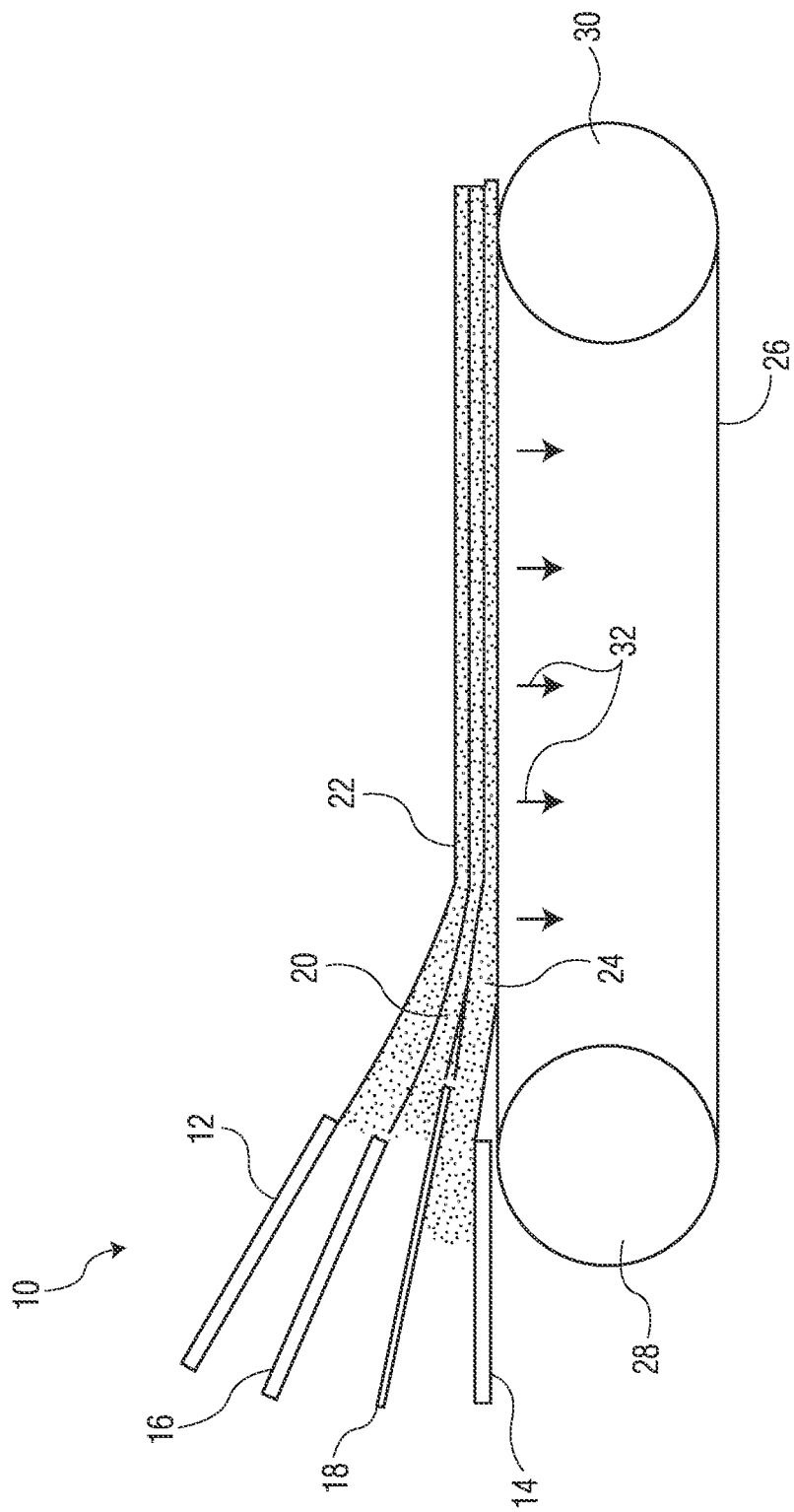
FIG. 1 illustrates one embodiment for forming a multi-layered tissue web according to the present invention.

As used herein the term "Basesheet" refers to a tissue web formed by any one of the papermaking processes described herein that has not been subjected to further processing, such as embossing, calendering, treatment with a binder or softening composition, perforating, plying, folding, or rolling into individual rolled products.

As used herein the term "Tissue Product" refers to products made from basesheets and includes, bath tissues, facial tissues, paper towels, industrial wipers, foodservice wipers, napkins, medical pads, and other similar products.

As used herein the term "Ply" refers to a discrete tissue web used to form a tissue product. Individual plies may be arranged in juxtaposition to each other.

As used herein, the term "Layer" refers to a plurality of strata of fibers, chemical treatments, or the like, within a ply. The term "Layered Tissue Web" generally refers to a tissue web formed from two or more layers of aqueous papermaking furnish. In certain instances, the aqueous papermaking furnish forming two or more of the layers comprise different fiber types.

As used herein the term "Basis Weight" generally refers to the conditioned weight per unit area of a tissue and is generally expressed as grams per square meter (gsm). Basis weight is measured as described in the Test Methods section below. While the basis weights of tissue products prepared according to the present invention may vary, in certain embodiments the products have a basis weight greater than about 20 gsm, such as greater than about 30 gsm, such as greater than about 40 gsm, such as from about 20 to about 80 gsm, such as from about 30 to about 60 gsm, such as from about 45 to about 55 gsm.

As used herein, the term "Caliper" refers to the thickness of a tissue product, web, sheet or ply, typically having units of microns (μm) and is measured as described in the Test Methods section below.

As used herein, the term "Sheet Bulk" refers to the quotient of the caliper (μm) divided by the bone dry basis weight (gsm). The resulting sheet bulk is expressed in cubic centimeters per gram (cc/g). Tissue products prepared according to the present invention may, in certain embodiments, have a sheet bulk greater than about 8.0 cc/g, more preferably greater than about 9.0 cc/g and still more preferably greater than about 10.0 cc/g, such as from about 8.0 to about 12.0 cc/g.

As used herein, the term "Slope" refers to the slope of the line resulting from plotting tensile versus stretch and is an output of the MTS TestWorks™ in the course of determining the tensile strength as described in the Test Methods section herein. Slope is reported in the units of grams (g) per unit of sample width (inches) and is measured as the gradient of the least-squares line fitted to the load-corrected strain points falling between a specimen-generated force of 70 to 157 grams (0.687 to 1.540 N) divided by the specimen width.

As used herein, the term "Geometric Mean Slope" (GM Slope) generally refers to the square root of the product of machine direction slope and cross-machine direction slope. While the GM Slope may vary amongst tissue products prepared according to the present disclosure, in certain embodiments, tissue products may have a GM Slope less than about 10.00 kg, more preferably less than about 9.00 kg and still more preferably less than about 8.00 g, such as from about 6.00 to about 10.0 g, such as from about 6.00 to about 8.00 kg.

As used herein, the term "Geometric Mean Tensile" (GMT) refers to the square root of the product of the machine direction tensile strength and the cross-machine direction tensile strength of the web. The GMT of tissue products prepared according to the present invention may vary, however, in certain instances the GMT may be about 700 g/3" or greater, such as about 800 g/3" or greater, such as about 900 g/3" or greater, such as from about 700 about 1,700 g/3", such as from about 800 to about 1,600 g/3", such as from about 900 to about 1,500 g/3".

As used herein, the term "Stiffness Index" refers to the quotient of the geometric mean tensile slope, defined as the square root of the product of the MD and CD slopes (having units of kg), divided by the geometric mean tensile strength (having units of grams per three inches).

Stiffness Index =

$$\frac{\sqrt{MD \text{ Tensile Slope (kg)} \times CD \text{ Tensile Slope (kg)}}}{GMT \text{ (g/3")}} \times 1{,}000$$

While the Stiffness Index of tissue products prepared according to the present disclosure may vary, in certain instances the Stiffness Index may be less than about 7.0, such as less than about 6.0, such as less than about 5.5, such as from about 4.0 to about 7.0, such as from about 4.0 to about 6.0.

As used herein, the term "TEA Index" refers the geometric mean tensile energy absorption (having units of g·cm/cm$^2$) at a given geometric mean tensile strength (having units of grams per three inches) as defined by the equation:

$$TEA \text{ Index} = \frac{GMTEA(\text{g} \cdot \text{cm}/\text{cm}^2)}{GMT(\text{g}/3")} \times 100$$

While the TEA Index may vary, in certain instances tissue products prepared according to the present disclosure have a TEA Index greater than about 1.50, such as greater than about 1.75, such as greater than about 2.00, such as from about 1.50 to about 2.25, such as from about 1.75 to about 2.25.

As used herein, the term "Slough" generally refers to the undesirable sloughing off of bits of the tissue web when rubbed and is generally measured as described in the Test Methods section below. Slough is generally reported in terms of mass, such as milligrams (mg). While the Slough of inventive tissue products may vary, in certain instances tissue products prepared according to the present invention have a Slough less than about 5.00 mg and more preferably less than about 4.00 mg, such as from about 0.50 to about 5.00, such as from about 0.50 to about 4.00 mg.

As used herein, the term "TS750" generally refers to the smoothness of a tissue product surface measured using an EMTEC Tissue Softness Analyzer ("Emtec TSA") (Emtec Electronic GmbH, Leipzig, Germany) interfaced with a computer running Emtec TSA software (version 3.19 or equivalent). The units of the TS750 value are dB $V^2$ rms, however, TS750 values are often referred to herein without reference to units. Generally, the TS750 value is the magnitude of the peak occurring at a frequency between about 200 and 1,000 Hz, which is produced by vibration of the tissue membrane during the test procedure. Such vibrations are mainly caused by roughness and embossing. Generally, a lower TS750 value is indicative of a smoother surface.

DETAILED DESCRIPTION

In general, the present disclosure is directed to creped tissue plies, and products produced therefrom. The creped plies and products are generally strong, flexible and have low amounts of Slough. For example, the invention provides tissue products having a Slough less than about 2.00 mg and more preferably less than about 1.50 mg, such as from about 0.20 to about 2.00, such as from about 0.50 to about 1.50 mg. Surprisingly, the foregoing Slough levels are achieved despite the product being creped and having a relatively high basis weight, such as greater than about 45 grams per square meter (gsm), such as from about 45 to about 60 gsm.

Figure 8:
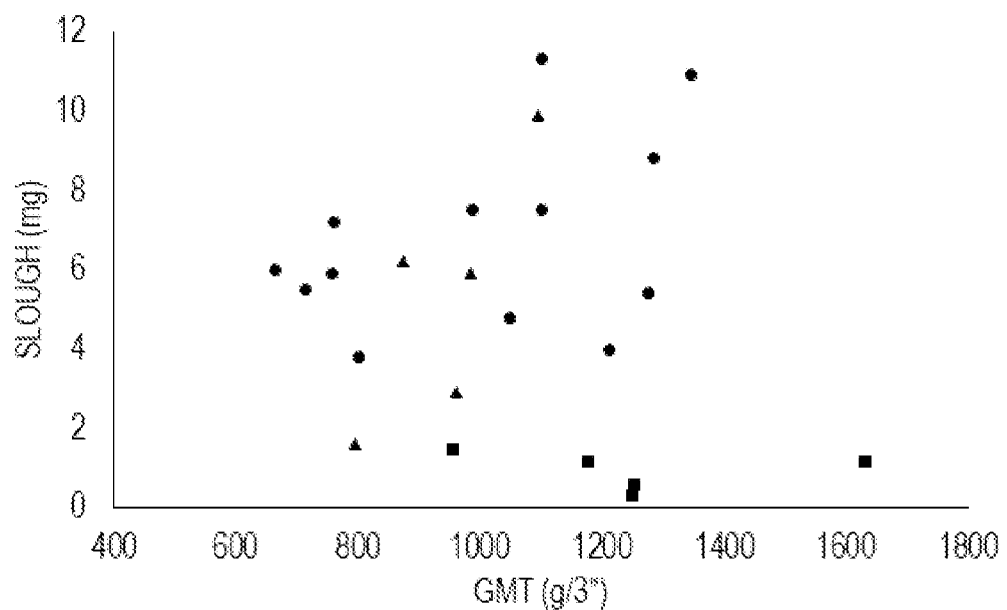
FIG. 8 is a graph of geometric mean tensile strength (GMT, g/3") versus Slough (mg) for commercial (●) and inventive (▲) products.
Figure 9:
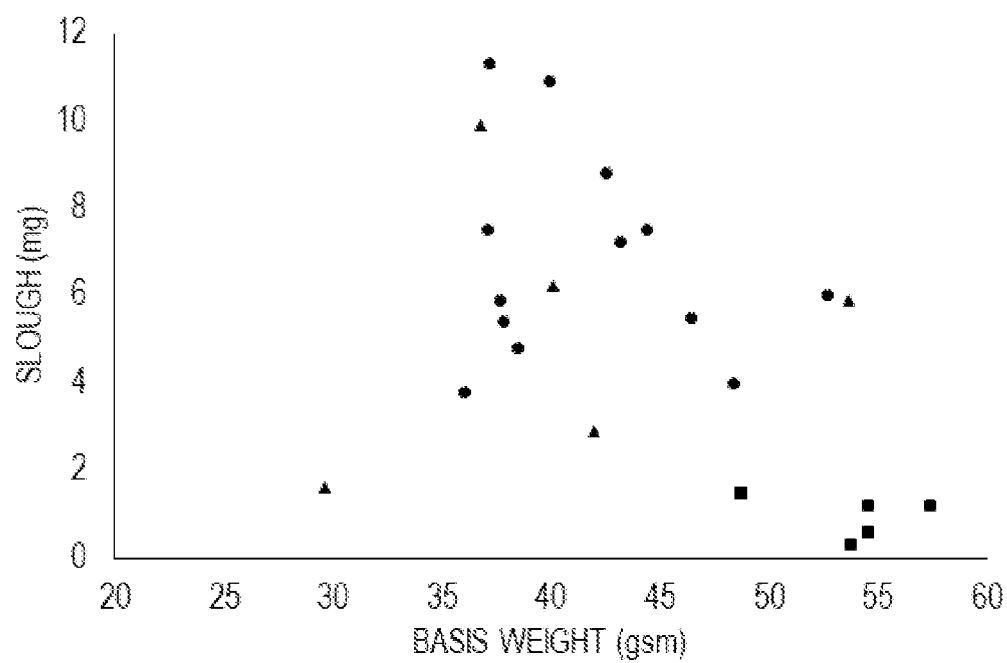
FIG. 9 is a graph of basis weight (gsm) versus Slough (mg) for commercial (■) and inventive (▲) products.

Typically, increased basis weight, and the often-associated higher web caliper, have a negative impact on creping resulting in higher Slough in the finished tissue product. A comparison of the Slough levels of several inventive and commercially available tissue products may be found in Table 1, below, and FIGS. 8 and 9. As shown in the table below, and in the attached figures, the inventive tissue products generally have a low amount of Slough, such as less than about 2.00 mg and more preferably less than about 1.50 mg, such as from about 0.20 to about 2.00, such as from about 0.50 to about 1.50 mg, despite being creped and having relatively high basis weights, such as greater than about 45 gsm, such as from about 45 to about 60 gsm.

TABLE 1

| Sample | Plies | Through-air Dried | Creped | Embossed | Basis Weight (gsm) | GMT (g/3") | Sheet Bulk (cc/g) | Slough (mg) |
| --- | --- | --- | --- | --- | --- | --- | --- | --- |
| Angel Soft | 2 | N | Y | Y | 37.7 | 758 | 8.9 | 5.9 |
| Charmin Sensitive | 2 | Y | Y | Y | 43.2 | 761 | 10.5 | 7.2 |
| Charmin Ultra Soft | 2 | Y | Y | Y | 46.5 | 715 | 11.3 | 5.5 |
| Charmin Ultra Strong | 2 | Y | Y | Y | 37.2 | 1102 | 12.6 | 11.3 |
| Cottonelle Ultra Comfort Care | 2 | Y | N | Y | 44.4 | 990 | 12.1 | 7.5 |
| Great Value Ultra Soft | 2 | Y | Y | Y | 38.5 | 1050 | 11.8 | 4.8 |
| Great Value Ultra Strong | 2 | Y | Y | Y | 40.0 | 1347 | 11.7 | 10.9 |
| Quilted Northern Ultra Plush | 3 | N | Y | Y | 52.7 | 665 | 9.5 | 6 |
| Quilted Northern Ultra Soft & Strong | 2 | N | Y | Y | 42.6 | 1286 | 11.2 | 8.8 |
| Target UP & Up Soft | 2 | Y | Y | Y | 36.1 | 802 | 8.2 | 3.8 |
| Target Up & Up Ultra Soft | 2 | Y | Y | Y | 37.1 | 1101 | 10.2 | 7.5 |
| White Cloud Ultra Bath Tissue | 2 | Y | Y | Y | 48.4 | 1212 | 7.6 | 4 |
| White Cloud Ultra Soft & Strong | 2 | Y | Y | Y | 37.9 | 1278 | 10.9 | 5.4 |
| Kleenex | 2 | N | Y | N | 29.7 | 797 | 6.0 | 1.6 |
| Puffs Plus Lotion | 2 | Y | Y | N | 40.1 | 874 | 7.2 | 6.2 |
| Kleenex Cool Touch | 2 | N | Y | N | 53.7 | 985 | 4.3 | 5.9 |
| Kleenex Lotion | 2 | N | Y | N | 42.0 | 962 | 4.9 | 2.9 |
| Puffs Ultra Soft and Strong | 2 | Y | Y | N | 36.8 | 1095 | 7.6 | 9.9 |
| Inventive 1 | 2 | Y | Y | Y | 54.6 | 1255 | 9.1 | 0.6 |
| Inventive 2 | 2 | Y | Y | Y | 53.8 | 1250 | 8.3 | 0.3 |
| Inventive 3 | 2 | Y | Y | Y | 57.4 | 1380 | 8.9 | 1.18 |

Despite this trend, the present invention surprisingly provides a high basis weight tissue product having low Slough. Accordingly, in one embodiment the present disclosure provides a creped tissue product, such as a multi-ply creped tissue product comprising two or more plies, having a geometric mean tensile (GMT) from about 700 to about 1,800 g/3", a basis weight from about 45 to about 60 gsm and a Slough less than about 2.00 mg, more preferably less than about 1.50 mg, such as from about 0.10 to about 2.00, such as from about 0.25 to about 1.50 mg.

In other embodiments tissue products prepared according to the present invention have desirable surface properties, such as a relatively high degree of surface smoothness. The inventive tissue products have good surface smoothness even in those instances where they are embossed. Thus, in certain embodiments, the present invention provides embossed tissue products having an embossing pattern that provides a visually appealing product with good bulk and a relatively smooth surface. For, example, the inventive tissue products may be embossed and have a TS750 value, which is one measurement of tissue product surface smoothness where a lower value indicates a smoother surface, less than about than 40.0 and more preferably less than about 30.0 and still more preferably less than about 25.0, such as from about 15.0 to 40.0, such as from about 20.0 to about 35.0.

Figure 10:
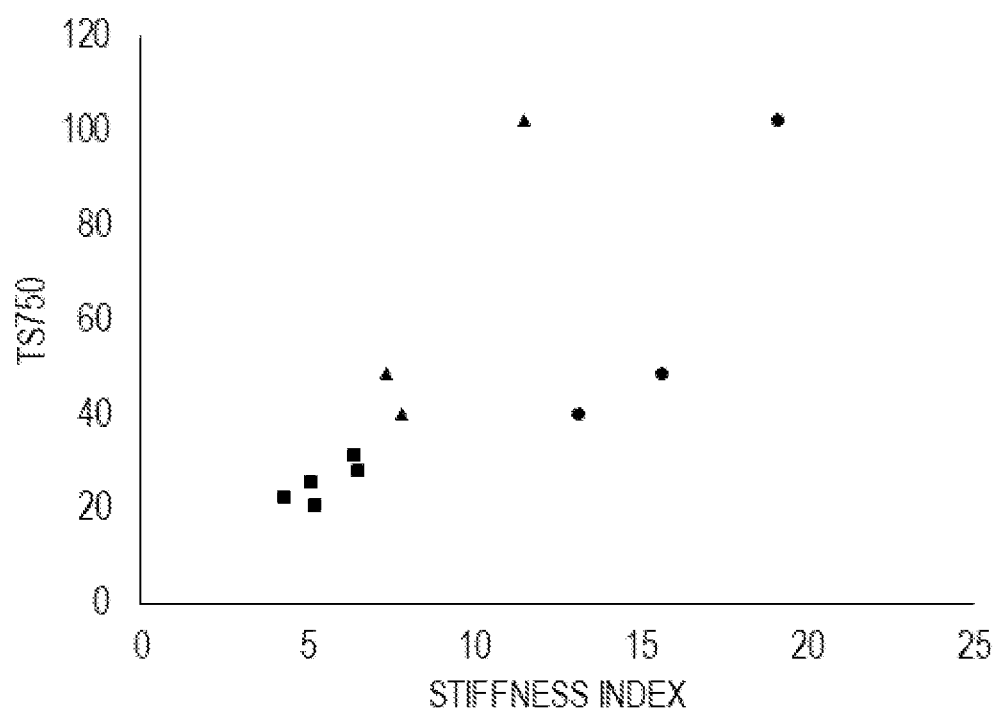
FIG. 10 is a graph of Stiffness Index versus TS750 for commercial (■) and inventive (▲) products.

In particularly preferred embodiments the tissue products comprise two or more creped tissue webs, wherein at least one of the webs is embossed, and wherein the product has a TS750 value less than about than 40.0 and more preferably less than about 30.0 and still more preferably less than about 25.0, such as from about 15.0 to about 40.0, such as from about 20.0 to about 35.0 and a sheet bulk greater than about 8.0 cc/g, such as from about 8.0 to about 12.0 cc/g. The foregoing TS750 values may be archived at relatively high degrees of strength and substance, such as a GMT from about 700 to about 1,800 g/3" and a basis weight from about 45 to about 60 gsm. A comparison of the surface smoothness of several inventive tissue products to commercially available tissue products may be found in Table 2, below, and FIGS. 9 and 10.

the first and second outer layers may comprise short, low coarseness wood pulp fibers, such as hardwood kraft pulp fibers, and the middle layer may comprise long, low coarseness wood pulp fibers, such as northern softwood kraft pulp fibers.

In those instances where the web comprises multiple layers, the relative weight percentage of each layer may vary. For example, the web may comprise first and second outer layers and a middle layer where the first outer layer comprises from about 25 to about 35 weight percent of the layered web, the middle layer comprises from about 30 to

TABLE 2

| Sample | Plies | Creped | Lotion | Embossed | Basis Weight (gsm) | GMT (g/3") | Stiffness Index | TS750 |
| --- | --- | --- | --- | --- | --- | --- | --- | --- |
| Charmin Ultra Gentle | 2 | Y | Y | Y | 43.6 | 786 | 7.86 | 40.0 |
| Charmin Sensitive | 2 | Y | Y | Y | 37.9 | 755 | 7.39 | 48.8 |
| Cottonelle Gentle Care | 1 | N | Y | N | 43.2 | 761 | 11.50 | 102.1 |
| Puffs Plus Lotion | 2 | Y | Y | N | 40.1 | 874 | 13.12 | 10.8 |
| Kleenex Lotion Facial Tissue | 2 | Y | Y | N | 42.0 | 962 | 15.63 | 17.9 |
| Kleenex Cooling Lotion Facial Tissue | 2 | Y | Y | N | 53.7 | 985 | 19.11 | 27.0 |
| Inventive 1 | 2 | Y | Y | Y | 54.6 | 1255 | 6.47 | 28.3 |
| Inventive 2 | 2 | Y | Y | Y | 53.8 | 1250 | 6.43 | 31.3 |
| Inventive 3 | 2 | Y | Y | Y | 57.4 | 1380 | 5.26 | 20.8 |

In still other embodiments the present invention provides a relatively flexible tissue product, such as a tissue product having a Stiffness Index less than about 8.0, such as from about 4.0 to about 8.0, such as from about 4.0 to about 7.0 and a high degree of surface smoothness, such as a TS750 value less than 40.0 and more preferably less than about 30.0 and still more preferably less than about 25.0, such as from about 15.0 to 40.0, such as from about 20.0 to about 35.0.

In a particularly preferred embodiment, the invention provides a multi-ply tissue product comprising at least a first and second creped tissue web, wherein the creped tissue webs comprise a non-crosslinked latex polymer disposed on at least one outer surface thereof. The tissue product may further comprise an embossing pattern to provide a visual aesthetic and to enhance the bulk of the product, such that the product has a sheet bulk greater than about 8.0 cc/g, such as greater than about 9.0 cc/g and more preferably greater than about 10.0 cc/g. The tissue product may also include a softening composition disposed on at least one of its outer surfaces, the softening composition comprising a softening compound selected from the group consisting of a polyhydroxy compound having a molecular weight of at least about 1,000 g/mol, a diamidoamine quaternary compound, an ester quaternary compound, an alkoxy alkyl quaternary compound, a benzyl quaternary compound, an alkyl quaternary compound, an imidazolinium quaternary compound, a polysiloxane, glycerin, and combinations thereof. Generally the foregoing product will have a high degree of surface smoothness, such as a TS750 value less than 40.0 and more preferably less than about 30.0 and a low level of Slough, such as such as a Slough less than about 2.00 mg and more preferably less than about 1.50 mg, such as from about 0.20 to about 2.00, such as from about 0.50 to about 1.50 mg, In certain embodiments tissue products may be formed from one or more basesheets, which may comprise a single homogenous or blended layer, or be multi-layered. In those instances where the basesheet is multi-layered it may comprise, two, three, or more layers. For example, the basesheet may comprise three layers such as first and second outer layers and a middle layer disposed there between. The layers may comprise the same or different fiber types. For example, about 50 weight percent of the layered web and the second outer layer comprises from about 25 to about 35 weight percent of the layered web.

Multi-layered basesheets useful in the present invention may be formed using any number of different processes known in the art, such as the process disclosed in U.S. Pat. No. 5,129,988, the contents of which are incorporated herein in a manner consistent with the present disclosure. One process for a forming multi-layered basesheet is illustrated in FIG. 1. A dilute aqueous suspension of papermaking fibers is dispersed from a headbox 10 having an upper headbox wall 12 and a lower headbox wall 14 and first and second dividers 16, 18. In this manner the headbox may be used to form a basesheet having outer layers 22, 24 and a middle layer 20, where each of the layers may comprise the same or different papermaking fibers.

To form the multi-layered basesheet, an endless traveling forming fabric 26, suitably supported and driven by rolls 28 and 30, receives the layered papermaking stock issuing from headbox 10. Once retained on fabric 26, the layered fiber suspension passes water through the fabric as shown by the arrows 32. Water removal is achieved by combinations of gravity, centrifugal force and vacuum suction depending on the forming configuration.

In certain embodiments the one or more layers of a multi-layered basesheet, such as the middle layer, may be formed without a substantial amount of inner fiber-to-fiber bond strength. In this regard, the fiber furnish used to form a given layer can be treated with a chemical debonding agent. The debonding agent can be added to the fiber slurry during the pulping process or can be added directly the fiber slurry prior to the headbox. Suitable debonding agents that may be used in the present invention include cationic debonding agents, particularly quaternary ammonium compounds, mixtures of quaternary ammonium compounds with polyhydroxy compounds, and modified polysiloxanes.

Suitable cationic debonding agents include, for example, fatty dialkyl quaternary amine salts, mono fatty alkyl tertiary amine salts, primary amine salts, imidazoline quaternary salts and unsaturated fatty alkyl amine salts. Other suitable debonding agents are disclosed in U.S. Pat. No. 5,529,665, the contents of which are incorporated herein in a manner consistent with the present disclosure. In one embodiment, the debonding agent used in the process of the present invention is an organic quaternary ammonium chloride, such as those available under the tradename ProSoft™ (Solenis, Wilmington, DE). The debonding agent can be added to the fiber slurry in an amount of from about 1.0 kg per metric tonne to about 15 kg per metric tonne of fibers present within the slurry.

Particularly useful quaternary ammonium debonders include imidazoline quaternary ammonium debonders, such as oleyl-imidazoline quaternaries, dialkyl dimethyl quaternary debonders, ester quaternary debonders, diamidoamine quaternary debonders, and the like. The imidazoline-based debonding agent can be added in an amount of between 1.0 to about 10 kg per metric tonne.

In other embodiments, a layer or other portion of the basesheet, including the entire basesheet, may optionally include wet or dry strength agents. As used herein, "wet strength agents" are materials used to immobilize the bonds between fibers in the wet state. Any material that when added to the tissue web at an effective level results in providing the basesheet with a wet geometric tensile strength:dry geometric tensile strength ratio in excess of 0.1 will, for purposes of this invention, be termed a wet strength agent. Particularly preferred wet strength agents are temporary wet strength agents. As used herein "temporary wet strength agents" are those which show less than 50 percent of their original wet strength after being saturated with water for five minutes.

Suitable temporary wet strength agents include materials that can react with hydroxyl groups, such as on cellulosic pulp fibers, to form hemiacetal bonds that are reversible in the presence of excess water. Suitable temporary wet strength agents are known to those of ordinary skill in the art. Non-limiting examples of temporary wet strength agents suitable for the fibrous structures of the present invention include glyoxalated polyacrylamide polymers, for example cationic glyoxalated polyacrylamide polymers. Temporary wet strength agents useful in the present invention may have average molecular weights of from about 20,000 to about 400,000, such as from about 50,000 to about 400,000, such as from about 70,000 to about 400,000, such as from about 70,000 to about 300,000, such as about 100,000 to about 200,000. In certain instances, the temporary wet strength agent may comprise a commercially available temporary wet strength agent such as those marketed under the tradename Hercobond™ (Solenis, Wilmington, DE) or Fenno-Bond™ (Kemira Chemicals, Inc., Atlanta, GA).

In other instances, the basesheet may optionally include a dry strength additive, such as carboxymethyl cellulose resins, starch based resins, and mixtures thereof. Particularly preferred dry strength additives are cationic starches, and mixtures of cationic and anionic starches. In certain instances, the dry strength agent may comprise a commercially available modified starch such as marketed under the tradename RediBOND™ (Ingredion, Westchester, IL) or a commercially available carboxymethyl cellulose resin such as those marketed under the tradename Aqualon™ (Ashland LLC, Bridgewater, NJ).

The amount of wet strength agent or dry strength added to the pulp fibers can be at least about 0.1 dry weight percent, more specifically about 0.2 dry weight percent or greater, and still more specifically from about 0.1 to about 3 dry weight percent, based on the dry weight of the fibers.

Tissue basesheets useful in forming tissue products of the present invention may be formed using any one of several well-known manufacturing processes. For example, in certain embodiments, tissue products may be produced by a through-air drying (TAD) manufacturing process, an advanced tissue molding system (ATMOS) manufacturing process, a structured tissue technology (STT) manufacturing process, a conventional wet pressed (also referred to as "CTEC") manufacturing process or a belt creped manufacturing process. In particularly preferred embodiments the tissue product is manufactured by a creped through-air dried (CTAD) process or uncreped through-air dried (UCTAD) process.

Figure 2:
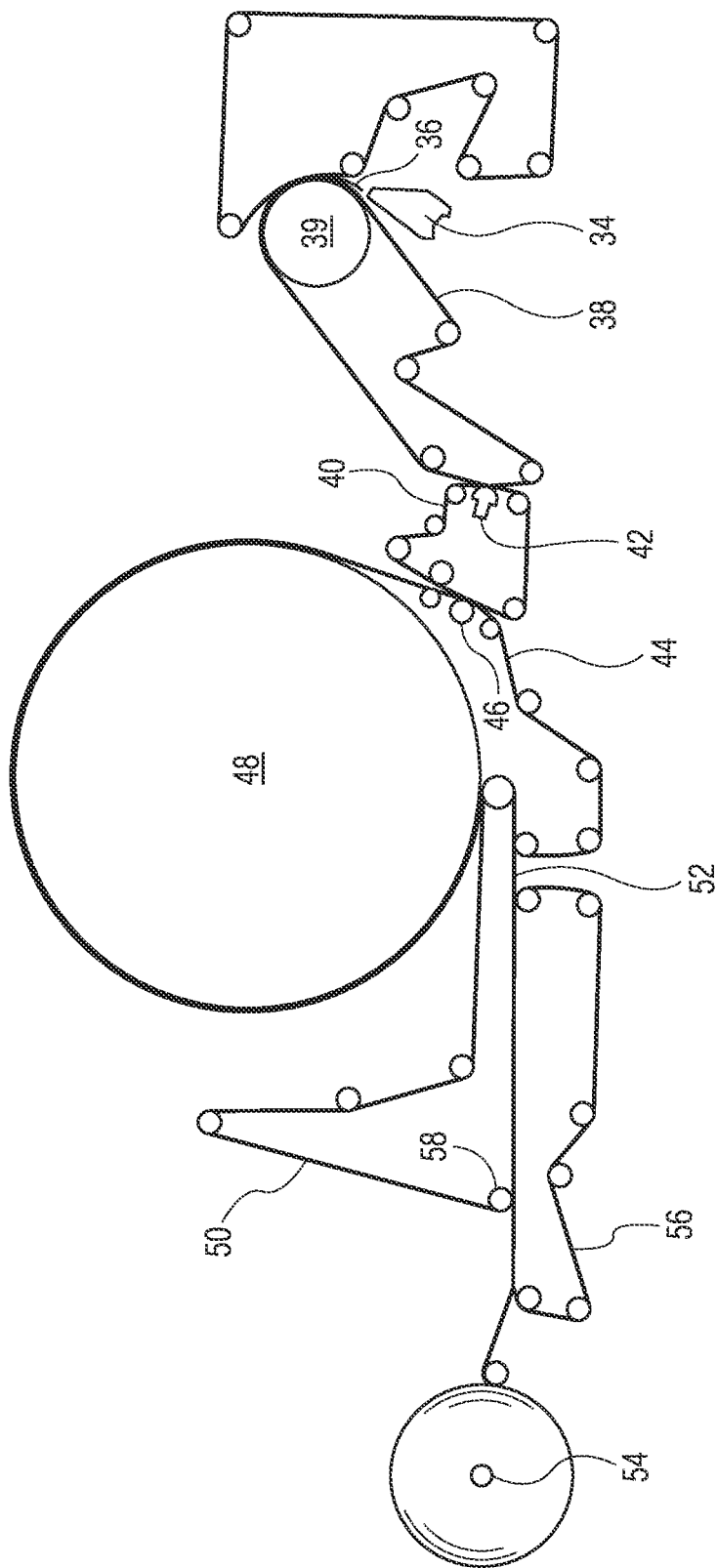
FIG. 2 illustrates one embodiment for forming a basesheet useful in the production of a tissue product according to the present invention.

With reference now to FIG. 2, a method for making through-air dried paper sheets is illustrated. Shown is a twin wire former having a papermaking headbox 34, such as a layered headbox, which injects or deposits a stream 36 of an aqueous suspension of papermaking fibers onto the forming fabric 38 positioned on a forming roll 39. The forming fabric serves to support and carry the newly-formed wet web downstream in the process as the web is partially dewatered to a consistency of about 10 dry weight percent. Additional dewatering of the wet web can be carried out, such as by vacuum suction, while the wet web is supported by the forming fabric.

The wet web is then transferred from the forming fabric to a transfer fabric 40. In one embodiment, the transfer fabric can be traveling at a slower speed than the forming fabric in order to impart increased stretch into the web. This is commonly referred to as a "rush" transfer. The relative speed difference between the two fabrics can be from 0 to 60 percent, more specifically from about 15 to 45 percent. Transfer is preferably carried out with the assistance of a vacuum shoe 42 such that the forming fabric and the transfer fabric simultaneously converge and diverge at the leading edge of the vacuum slot.

The web is then transferred from the transfer fabric to the through-air drying fabric 44 with the aid of a vacuum transfer roll 46 or a vacuum transfer shoe, optionally again using a fixed gap transfer as previously described. The through-air drying fabric can be traveling at about the same speed or a different speed relative to the transfer fabric. If desired, the through-air drying fabric can be run at a slower speed to further enhance stretch. Transfer can be carried out with vacuum assistance to ensure deformation of the sheet to conform to the through-air drying fabric, thus yielding desired bulk and imparting the web with a three-dimensional topographical pattern. Suitable through-air drying fabrics are described, for example, in U.S. Pat. Nos. 6,998,024, 7,611,607 and 10,161,084, the contents of which are incorporated herein by reference in a manner consistent with the present disclosure.

In one embodiment, the through-air drying fabric comprises a single layer fabric woven from shute and warp filaments. In certain instances, the shute filaments may comprise two or more different diameters and may be interwoven with the warp filaments so as to form a textured sheet contacting surface having substantially continuous machine-direction ripples separated by valleys. In other instances, the woven fabric may comprise a plurality of substantially continuous machine-direction ripples formed of multiple warp strands grouped together and supported by multiple shute strands of two or more diameters. During drying, the web can be macroscopically arranged to conform to the surface of the through-air drying fabric and form a textured, three-dimensional surface.

The side of the web contacting the through-air drying fabric is typically referred to as the "fabric side" of the paper web. The fabric side of the paper web, as described above, may have a shape that conforms to the surface of the through-air drying fabric after the fabric is dried in the through-air dryer. The opposite side of the paper web, on the other hand, is typically referred to as the "air side."

The level of vacuum used for the web transfers can be from about 3 to about 15 inches of mercury (75 to about 380 millimeters of mercury), preferably about 5 inches (125 millimeters) of mercury. The vacuum shoe (negative pressure) can be supplemented or replaced by the use of positive pressure from the opposite side of the web to blow the web onto the next fabric in addition to or as a replacement for sucking it onto the next fabric with vacuum. Also, a vacuum roll or rolls can be used to replace the vacuum shoe(s).

While supported by the through-air drying fabric, the web is dried to a consistency of about 94 percent or greater by the through-air dryer 48 and thereafter transferred to a carrier fabric 50. The dried basesheet 52 is transported to the reel 54 using carrier fabric 50 and an optional carrier fabric 56. An optional pressurized turning roll 58 can be used to facilitate transfer of the web from carrier fabric 50 to fabric 56.

In one embodiment, the reel 54 shown in FIG. 2 can run at a speed slower than the fabric 56 in a rush transfer process for building bulk into the paper web 52. For instance, the relative speed difference between the reel and the fabric can be from about 5 to about 25 percent and, particularly from about 12 to about 14 percent. Rush transfer at the reel can occur either alone or in conjunction with a rush transfer process upstream, such as between the forming fabric and the transfer fabric.

Once the web is formed, a binder composition is applied to at least one side of the web. In this manner, the present invention provides a tissue product comprising a web having first and second outer surfaces, wherein at least one outer surface comprises a topically-applied binder, particularly a binder applied in a network. As used herein, the term "network" is used to describe any binder pattern that serves to bond the sheet together. The pattern can be regular or irregular and can be continuous or discontinuous.

Figure 3:
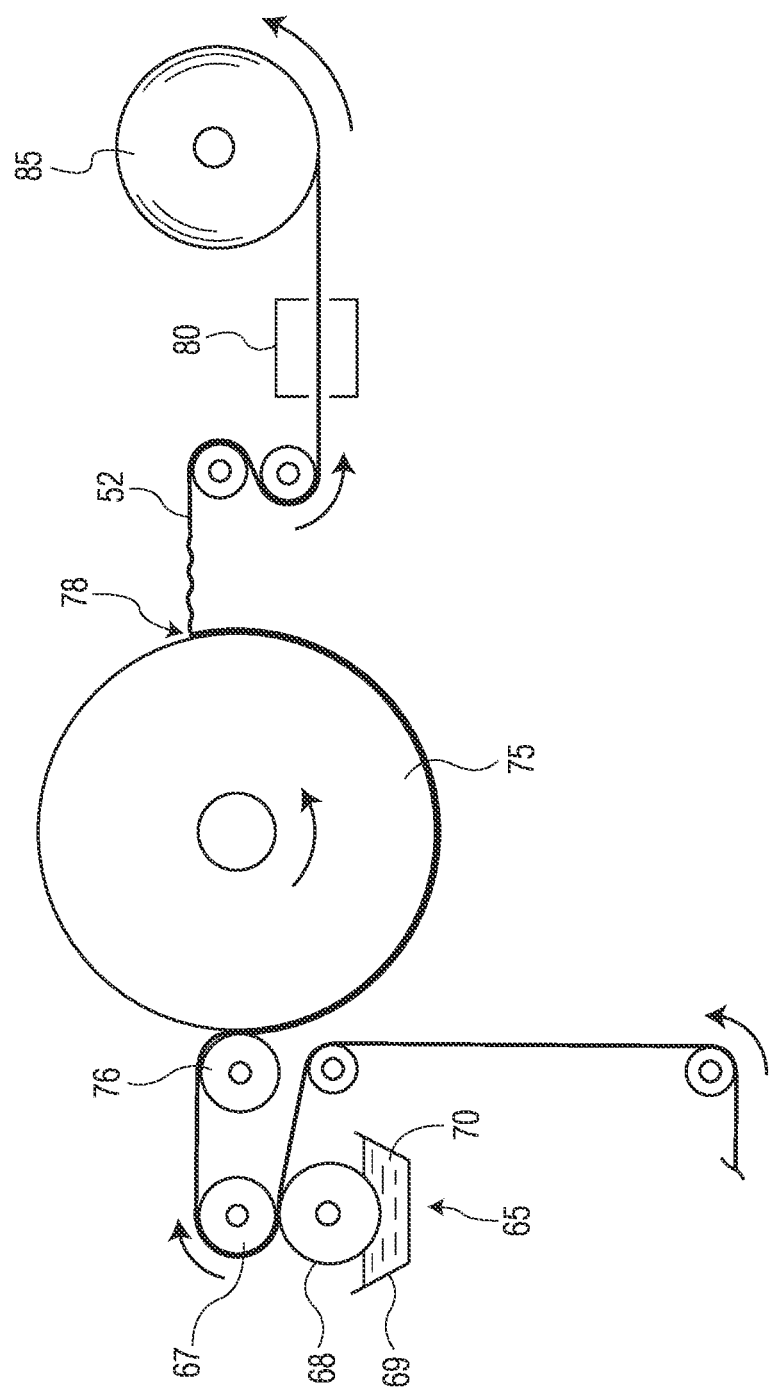
FIG. 3 illustrates one embodiment of a print-crepe process for producing a tissue product according to the present invention.

With reference now to FIG. 3, one embodiment of applying a binder material to one outer surface of a web is illustrated. Shown is paper web 52 passing through a binder material application station 65. Station 65 includes a transfer roll 67 in contact with a rotogravure roll 68, which is in communication with a reservoir 69 containing a suitable binder 70. Although gravure printing of the binder is illustrated, other means of applying the binder material can also be used, such as foam application, spray application, flexographic printing, or digital printing methods, such as ink jet printing, and the like. The rotogravure roll 68 applies binder material 70 to one side of the web 52 in a pre-selected pattern.

Figure 4:
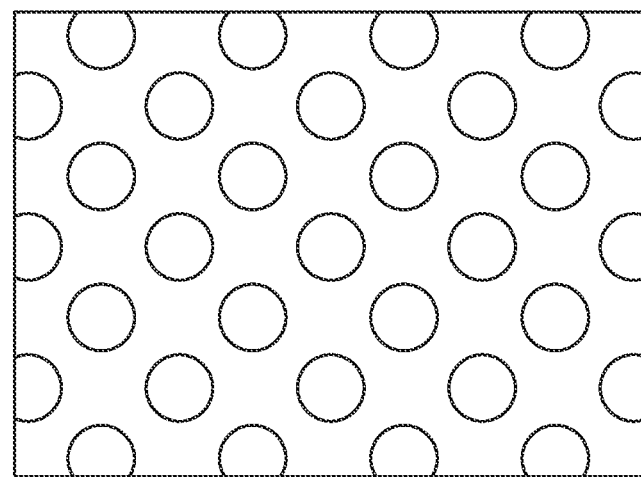
FIG. 4 illustrates one pattern for applying a binder to a basesheet.
Figure 5:
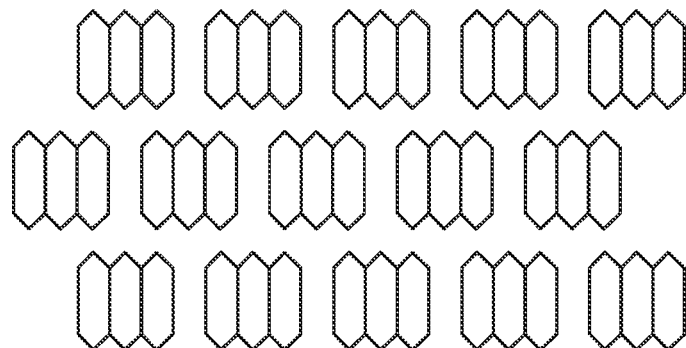
FIG. 5 illustrates another pattern for applying a binder to a basesheet.
Figure 6:
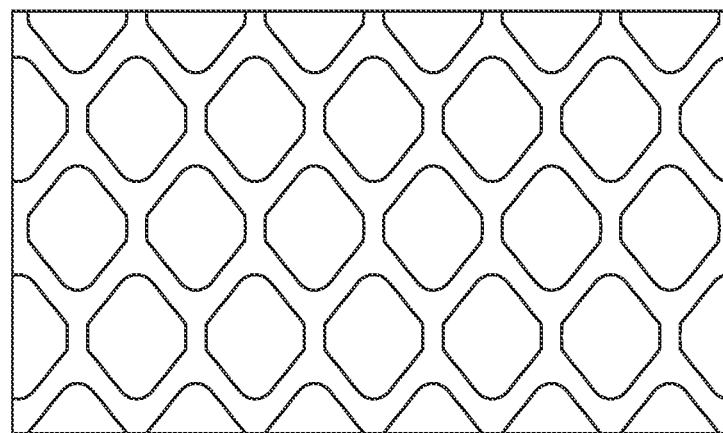
FIG. 6 illustrates still another pattern for applying a binder to a basesheet.

FIGS. 4-6 illustrate several different print patterns that may be used for applying a binder material to a basesheet in accordance with this invention. As illustrated in FIG. 4, the pattern may comprise a succession of discrete dots. In one embodiment, for instance, the dots can be spaced so that there are approximately from about 25 to about 35 dots per inch (25.4 mm) in the machine direction and/or the cross-machine direction. The dots can have a diameter, for example, of from about 0.01 inch (0.25 mm) to about 0.03 inch (0.76 mm). In one particular embodiment, the dots can have a diameter of about 0.02 inch (0.51 mm) and can be present in the pattern so that approximately 28 dots per inch (25.4 mm) extend in both the machine direction and the cross-machine direction. Besides dots, various other discrete shapes such as elongated ovals or rectangles can also be used when printing the binder material onto the sheet.

FIG. 5 shows a print pattern in which the binder material print pattern is made up of discrete multiple deposits that are each comprised of three elongated hexagons. In one embodiment, each hexagon can be about 0.02 inch (0.51 mm) long and can have a width of about 0.006 inch (0.15 mm). Approximately 35 to 40 deposits per inch (25.4 mm) can be spaced in the machine direction and the cross-machine direction.

FIG. 6 illustrates an alternative binder material pattern in which the binder material is printed onto the sheet in a reticulated pattern. The dimensions are similar to those of the dot pattern of FIG. 4. Reticulated patterns, which provide a continuous network of binder material, may result in relatively greater sheet strength than comparable patterns of discrete elements, such as the dot pattern of FIG. 4. It will be appreciated that many other patterns, in addition to those illustrated above, can also be used depending on the desired properties of the final product.

With reference again to FIG. 3, after the binder material 70 is applied, the sheet 52 is adhered to a heated creping cylinder 75 by a press roll 76. The sheet 52 is carried on the surface of the heated creping cylinder 75 for a distance and then removed therefrom by the action of a creping blade 78. The creping blade 78 performs a controlled pattern creping operation on the side of the sheet 52 to which the binder material 70 was applied.

Once creped, the sheet 52 is pulled through an optional drying station 80. The drying station can include any form of a heating unit, such as an oven energized by infrared heat, microwave energy, hot air, or the like. Alternatively, the drying station may comprise other drying methods such as photo-curing, UV-curing, corona discharge treatment, electron beam curing, curing with reactive gas, curing with heated air such as through-air heating or impingement jet heating, infrared heating, contact heating, inductive heating, microwave or RF heating, and the like. Depending upon the binder material selected, however, drying station 80 may not be needed. Once passed through the drying station 80, the sheet 52 can be wound into a roll of material or product 85.

In certain instances, the binder composition may be selected not only to assist in creping the web but also for improving one or more physical properties of the web such as, for example, dry strength, wet strength, stretchability, and tear resistance. Particular binder compositions that may be used in the present invention include latex compositions. The latex composition may comprise a non-carboxylated latex emulsion or a carboxyl-functional latex emulsion polymer. Non-carboxylated latex emulsions useful in the present invention may comprise an aqueous polymer dispersion of vinyl acetate and ethylene. Suitable non-carboxylated latex emulsions include vinyl acetate and ethylene emulsions such as Vinnapas™ EZ123, commercially available from Wacker Polymers, LP (Allentown, PA). In other instances, the binder composition may comprise a carboxyl-functional latex polymer such as Vinnapas™ EP1133, commercially available from Wacker Polymers, LP (Allentown, PA).

Latex polymers useful in the present invention may comprise unsaturated monomers, such as vinyl acetate and ethylene monomers, polymerized in the presence of surfactants and initiators to produce emulsion-polymerized polymer particles. Unsaturated monomers contain carbon-to-carbon double bond unsaturation and generally include vinyl monomers, styrenic monomers, acrylic monomers, allylic monomers, acrylamide monomers, as well as carboxyl functional monomers. Vinyl monomers include vinyl esters such as vinyl acetate, vinyl propionate and similar vinyl lower alkyl esters, vinyl halides, vinyl aromatic hydrocarbons such as styrene and substituted styrenes, vinyl aliphatic monomers such as alpha olefins and conjugated dienes, and vinyl alkyl ethers such as methyl vinyl ether and similar vinyl lower alkyl ethers. Acrylic monomers include lower alkyl esters of acrylic or methacrylic acid having an alkyl ester chain from one to twelve carbon atoms as well as aromatic derivatives of acrylic and methacrylic acid. Useful acrylic monomers include, for instance, methyl, ethyl, butyl, and propyl acrylates and methacrylates, 2-ethyl hexyl acrylate and methacrylate, cyclohexyl, decyl, and isodecyl acrylates and methacrylates, and similar various acrylates and methacrylates.

In certain embodiments the latex polymers may comprise a carboxyl-functional latex polymer comprising copolymerized carboxyl-functional monomers such as acrylic and methacrylic acids, fumaric or maleic or similar unsaturated dicarboxylic acids, where the preferred carboxyl monomers are acrylic and methacrylic acid. In certain instances, the carboxyl-functional latex polymers may comprise by weight from about 1 to about 50 percent copolymerized carboxyl monomers with the balance being other copolymerized ethylene monomers. Suitable carboxyl-functional latex polymers include carboxylated vinyl acetate-ethylene polymer emulsions such as Vinnapas™ EP1133, commercially available from Wacker Polymers, LP (Allentown, PA).

In certain instances, the binder composition may optionally contain an anti-blocking additive designed to modify the surface chemistry or characteristics of the binder film on the basesheet. Suitable anti-blocking additives generally do not react chemically with the binder and may include: 1) surfactants, including anionic surfactants such as sodium and potassium salts of stearic, palmitic, oleic, lauric, and tall oil fatty acids, and non-ionic surfactants such as polyoxyethylene glycols reacted to a lyophilic compound; 2) non-reactive additives, such as silicones, waxes, oils, designed to modify the surface chemistry of at least one outer surface of the web to reduce blocking; and 3) soluble or insoluble crystals, such as sugars, talc, clay, and the like, designed to reside on the surface of the binder film and thus reduce its propensity to cause blocking to an adjacent web surface. The amount of the anti-blocking additive in the binder composition, relative to the amount of carboxyl-functional latex emulsion polymer on a weight percent solids basis, can be from about 1 to about 25 percent, more specifically from about 5 to about 20 percent and more specifically from about 10 to about 15 percent.

Accordingly, in certain embodiments, binders useful in the present invention may consist essentially of a non-crosslinked latex polymer, such as a vinyl acetate-ethylene latex polymer, and optionally an anti-blocking agent, such as a polysaccharide, to prevent blocking upon drying of the tissue web.

In certain preferred embodiments it may be desirable to form the inventive tissue products using a binder that is substantially free from polyfunctional aldehydes, such as glyoxalated polyacrylamide and glyoxal, and azetidinium-functional cross-linking polymers, such as polyamide-epichlorohydrin (PAE) resins and polyamide-polyamine-epichlorohydrin (PPE) resins. Thus, in a preferred embodiment the latex polymer, which may comprise either a non-carboxylated or a carboxylated latex polymer, is not subjected to crosslinking before or after it is applied to the tissue web.

In certain instances, the binder composition may be applied to the base web in a preselected pattern. In one embodiment, for instance, the binder composition can be applied to the web in a reticular pattern, such that the pattern is interconnected forming a net-like design or grid on the surface. In other embodiments the binder composition may be applied to the web in a pattern that represents a succession of discrete shapes. For example, the binder composition may be applied in a pattern of discrete dots. Despite consisting of discrete shapes, such patterns provide the desired physical properties without covering a substantial portion of the surface area of the web.

In certain preferred embodiments the binder composition is applied to only one side of the web so as to cover from about 15 to about 75 percent of the surface area of the web. More particularly, in most applications, the binder composition will cover from about 20 to about 60 percent of the surface area of the web. The total amount of binder composition applied to the web can be in the range of from about 1 to about 25 percent by weight, such as from about 2 to about 10 percent by weight, based upon the total weight of the web.

In the embodiment shown in FIG. 3 only one side of the web is treated with a binder composition leaving an untreated side. Leaving one side of the tissue web untreated may provide various benefits and advantages under some circumstances. For instance, the untreated side may increase the ability of the tissue web to absorb liquids faster. Further, the untreated side may have a greater texture than if the side were treated with a binder composition.

Further, the process illustrated in FIG. 3 represents only one possible method for applying a binder composition to the web. Other applications methods may be suitable for applying a binder composition to the web. For example, various printing methods can be used to print the binder composition onto the web depending upon the particular application. Such printing methods can include direct gravure printing, offset gravure printing, or flexographic printing.

In addition to having a binder composition applied to one or more outer surfaces, as described above, the tissue product may be subjected to additional converting, such as calendering, treatment with a softening composition, embossing, slitting, winding and/or folding.

In certain embodiments tissue products of the present invention may be treated with a softening composition to improve the hand feel or deliver a benefit to the end user. As used herein, the term "softening composition" refers to any chemical composition which improves the tactile sensation perceived by the end user who holds a particular tissue product and rubs it across the skin. Suitable softening compositions include, for example, basic waxes such as paraffin and beeswax and oils such as mineral oil and silicone oil as well as petrolatum and more complex lubricants and emollients such as quaternary ammonium compounds with long alkyl chains, functional silicones, fatty acids, fatty alcohols and fatty esters.

Accordingly, in one embodiment the tissue products of the present invention may be treated with a softening composition comprising one or more oils, such as mineral oil, waxes, such as paraffin, or plant extracts, such as chamomile and aloe vera, such as disclosed in U.S. Pat. Nos. 5,885,697 and 5,525,345, the contents of which are incorporated herein in a manner consistent with the present disclosure.

In other embodiments the tissue products may be treated with a softening composition comprising a polysiloxane, and more preferably with a composition comprising an amino-functional polysiloxane, a surfactant and optionally a skin conditioning agent, such as the compositions disclosed in U.S. Publication No. 2006/0130989, the contents of which are incorporated herein in a manner consistent with the present disclosure. In certain preferred embodiments the polysiloxane is an amino-functional polysiloxane, the surfactant is an ethoxylated alcohol or an ethoxylated propoxylated alcohol and the skin conditioning agent is vitamin E and/or aloe vera.

In still other embodiments the tissue products may be treated with a softening composition comprising a cationic softening compound and a relatively high molecular weight polyhydroxy compound. Suitable cationic softening compounds include both quaternary ammonium compounds including, for example, amidoamine quaternary ammonium compounds, diamidoamine quaternary ammonium compounds, ester quaternary ammonium compounds, alkoxy alkyl quaternary ammonium compounds, benzyl quaternary ammonium compounds, alkyl quaternary ammonium compounds, and imidazolinium compounds. Examples of polyhydroxy compounds useful in the present invention include, but are not limited to, polyethylene glycols and polypropylene glycols having a molecular weight of at least about 1,000 g/mol and more preferably greater than about 2,000 g/mol and still more preferably greater than about 4,000 g/mol and more preferably greater than about 6,000 g/mol, such as from about 1,000 to about 12,000 g/mol, and more preferably from about 4,000 to about 10,000 g/mol and still more preferably from about 6,000 to about 8,000 g/mol.

In yet other embodiments the softening composition may comprise a cationic softening compound, a relatively high molecular weight polyhydroxy compound and polysiloxane. Any polysiloxane capable of enhancing the tactile softness of the tissue sheet is suitable for incorporation in this manner so long as solutions or emulsions of the cationic softener, polyhydroxy and silicone are compatible, that is when mixed they do not form gels, precipitates or other physical defects that would preclude application to the tissue sheet.

In other embodiments softening compositions useful in the present invention may consist essentially of water, a cationic softening compound, such as a quaternary ammonium compound, a polyhydroxy compound having a molecular weight of at least about 1,000 g/mol and optionally a silicone or glycerin, or mixtures thereof. In other embodiments the softening composition may consist essentially of water, a quaternary ammonium compound, a polyhydroxy compound having a molecular weight of at least about 1,000 g/mol, a silicone and glycerin. When incorporated in the softening composition, the amount of glycerin in the softening composition can be from about 5.0 to about 40 weight percent, more particularly from about 10 to about 30 weight percent, and still more particularly from about 15 to about 20 weight percent.

All of the foregoing softening compositions may optionally contain a beneficial agent, such as a skin conditioning agent or a humectant, which may be provided in an amount ranging from about 0.01 to about 5 percent by weight of the composition. Suitable humectants include lactic acid and its salts, sugars, ethoxylated glycerin, ethoxylated lanolin, corn syrup, hydrolyzed starch hydrolysate, urea, and sorbitol. Suitable skin conditioning agents include allantoin, kaolin, zinc oxide, aloe vera, vitamin E, petrolatum and lanolin. Again, the foregoing additives are generally complementary to the softening compositions of the present invention and generally do not significantly and adversely affect important tissue product properties, such as strength or absorbency of the tissue product, or negatively affect the softening provided by the softening compositions of the present invention.

The foregoing softening compositions are generally applied to one or two outermost surfaces of a dry tissue web and more preferably a creped tissue web having a binding composition disposed on at least one outer surface. The method by which the softening composition is applied to the tissue sheet may be accomplished by any method known in the art. For example, in one embodiment the composition may be applied by contact printing methods such as gravure, offset gravure, flexographic printing, and the like. The contact printing methods often enable topical application of the composition to the tissue sheet. In other embodiments the softening composition may be applied to the tissue web by non-contact printing methods such as ink jet printing, digital printing of any kind, and the like.

In certain preferred embodiments the softening composition may be prepared as an aqueous solution and applied to the web by spraying or rotogravure printing. It is believed in this manner that tactile softness of the tissue sheet and resulting tissue products may be improved due to presence of the softening composition on the surface of the tissue product. When applied as an aqueous solution, the softening composition may comprise from about 50 to about 90 weight percent, by weight of the composition, water and more preferably from about 60 to about 80 percent.

In other instances, the basesheets prepared as described above may be subjected to embossing and plying to produce the inventive tissue products. For example, the tissue products of the present invention may be provided as multi-ply products comprising two or more plies, such as two, three or four plies, where the plies are embossed and laminated together. In one embodiment, the multi-ply product of the present invention may be produced using an embossing-laminating device, such as those described in U.S. Pat. Nos. 3,556,907, 3,867,225 and 5,339,730, the contents of which are incorporated herein in a manner consistent with the present disclosure. For example, two plies may be embossed separately, each between an embossing roller and a counter-roller or pressure roller. The two plies may then be brought into facing relation with one another and joined so that the protuberances of one ply are nested between the protuberances of the other ply. Typically, lamination of the two plies is obtained between one of the embossing rollers and a laminating roller, while the two embossing rollers do not touch.

TEST METHODS

Basis Weight

Prior to testing, all samples are conditioned under TAPPI conditions (23±1° C. and 50±2 percent relative humidity) for a minimum of 4 hours. Basis weight of sample is measured by selecting twelve (12) products (also referred to as sheets) of the sample and making two (2) stacks of six (6) sheets. In the event the sample consists of perforated sheets of bath or towel tissue, the perforations must be aligned on the same side when stacking the usable units, A precision cutter is used to cut each stack into exactly 10.16×10.16 cm (4.0×4.0 inch) squares. The two stacks of cut squares are combined to make a basis weight pad of twelve (12) squares thick. The basis weight pad is then weighed on a top loading balance with a minimum resolution of 0.01 grams. The top loading balance must be protected from air drafts and other disturbances using a draft shield. Weights are recorded when the readings on the top loading balance become constant. The mass, of the sample (grams) per unit area (square meters) is calculated and reported as the basis weight, having units of grams per square meter (gsm).

Caliper

Caliper is measured in accordance with TAPPI test methods Test Method T 580 pm-12 "Thickness (caliper) of towel, tissue, napkin and facial products." The micrometer used for carrying out caliper measurements is an Emveco 200-A Tissue Caliper Tester (Emveco, Inc., Newberg, OR). The micrometer has a load of 2 kilo-Pascals, a pressure foot area of 2,500 square millimeters, a pressure foot diameter of 56.42 millimeters, a dwell time of 3 seconds and a lowering rate of 0.8 millimeters per second.

Slough

The Slough test provides a quantitative measure of the abrasion resistance of a tissue sample. More specifically, the test measures the resistance of a material to an abrasive action when the material is subjected to a horizontally reciprocating surface abrader. The equipment used to measure Slough is similar to that described in U.S. Pat. No. 6,808,595, the disclosure of which is incorporated by reference herein in a manner consistent with the present invention. The abrading spindle consists of a stainless-steel rod, approximately 1.25 cm (0.495 inches) in diameter and 15.25 cm (6 inches) in length. The abrasive portion of the abrading spindle is 10.8 cm (4.25 inches) in length and consists of 18/22 abrasion coating (commercially available from Superabrasives, Inc., Wixom, MI) applied around the entire circumference of the abrading spindle. The abrading spindle is mounted perpendicularly to the face of the instrument such that the abrasive portion of the abrading spindle extends out its entire distance from the face of the instrument. On each side of the abrading spindle is located a pair of clamps, one movable and one fixed. The clamps are spaced 10 cm (4 inches) apart and centered about the abrading spindle. The movable clamp (weighing approximately 21 grams) is allowed to slide freely in the vertical direction, the weight of the movable clamp providing the means for ensuring a constant tension of the tissue sheet sample over the surface of the abrading spindle. Instruments for measuring Slough according to the present invention are available at Accelerated Analytical Laboratories (Milwaukee, WI).

Prior to testing, any loose dust should be removed from the abrading spindle with compressed air. If other debris is present on the abrading spindle, the spindle may be washed in warm water and dish detergent, rinsed with distilled water and dried in an oven. In the event the abrading spindle is washed prior to use, care must be taken to ensure that all cleaning solution is rinsed from the abrading spindle and that it is completely dry before use.

Figure 7:
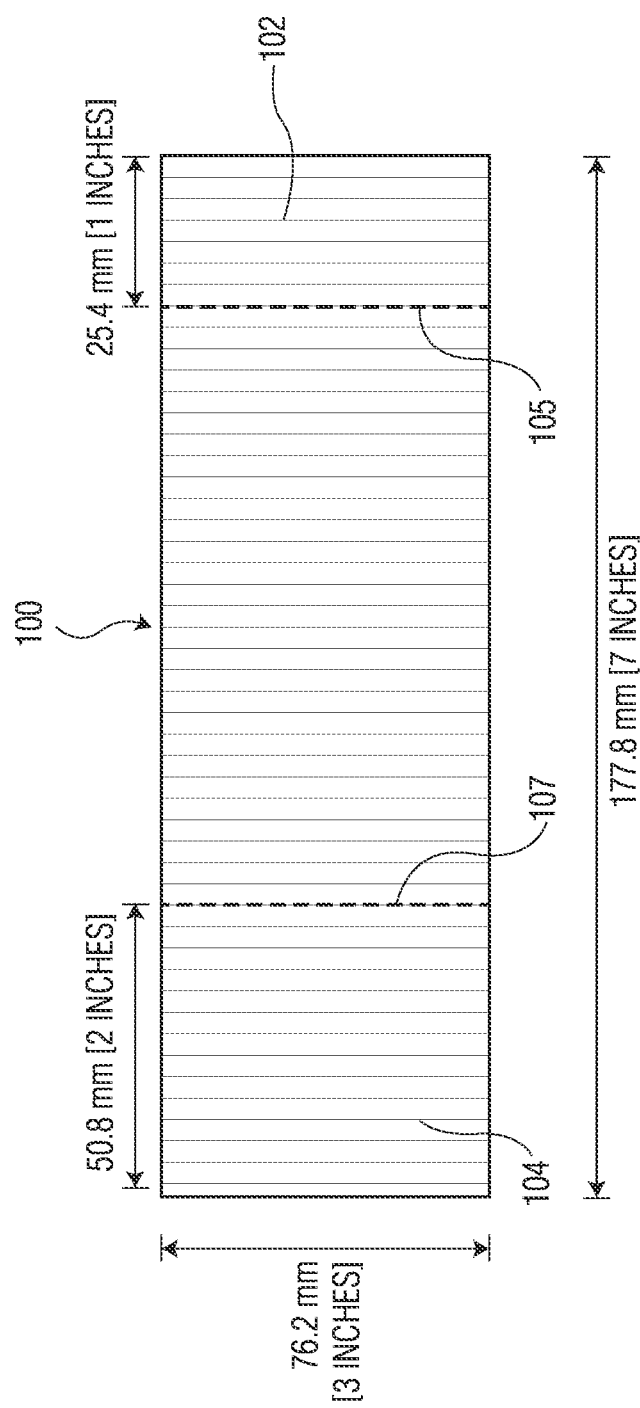
FIG. 7 illustrates a test specimen prepared for Slough testing.

Samples are conditioned under TAPPI conditions (23±1° C. and 50±2 percent relative humidity) for a minimum of 4 hours prior to testing. For perforated bath tissue products, samples are first prepared by unrolling the tissue and separating into lengths of 3 sheets. Using a precision cutter, such as a JDC-3 cutter (commercially available from Thwing-Albert Instrument Company, Philadelphia, PA), each sample is cut to a size of 177.8±13 mm (7.0±0.5 inches) in the machine direction (MD) by 76.2±1 mm (3.0±0.04 inches) in the cross-machine direction (CD). When cutting perforated bath tissue products, as illustrated in FIG. 7, the sample 100 is cut such that a first end 102 extends 25.4 mm (1 inch) beyond a first line of perforations 105 and a second end 104 extends 50.8 mm (2 inches) beyond a second line of perforations 107 to ensure that the spindle does not abrade over the perforations 105, 107 in the sample 100.

When testing rolled and perforated bath tissue products testing should be done on the outside surface of the roll as it is unwound. Generally rolled and perforated bath tissue products are not separated into individual plies prior to testing and the outer surface of the product, as it is unwound from the roll, is tested. When testing folded facial tissue products, the product is separated into individual plies and the outward facing side of one of the outer plies is tested.

Each tissue sheet sample is weighed to the nearest 0.1 mg. One end of the tissue sheet sample is clamped to the fixed clamp, the sample is then loosely draped over the abrading spindle and clamped into the sliding clamp. The entire width of the sample should be in contact with the abrading spindle. The sliding clamp is then allowed to fall providing constant tension across the abrading spindle. The entire width of the tissue sheet sample should be in contact with the abrading spindle.

Once the sample is secured the test begins by moving the abrading spindle back and forth at an approximate 15-degree angle from the centered vertical centerline in a reciprocal horizontal motion against the tissue sample for 40 cycles at a speed of 73.5±0.5 cycles per minute. As the spindle cycles, it is also rotated counterclockwise (when looking at the front of the instrument) at an approximate speed of 5 RPMs. Once the 40 cycles are complete, the tissue sample is removed from the jaws with the fingertips and both sides of the sample are blown with air having a flow rate of approximately 3.4 scfm for approximately 13 seconds to remove debris.

The tissue sheet sample is then weighed to the nearest 0.1 mg and the weight loss calculated. The difference between the initial weight and the weight after testing is the amount of Slough. Ten samples are tested and the average weight loss value in milligrams (mg) is recorded, which is the Slough value for the sample.

Burst Strength (Wet or Dry)

Burst Strength is measured using an EJA Burst Tester (series #50360, commercially available from Thwing-Albert Instrument Company, Philadelphia, PA). The test procedure is according to TAPPI T570 pm-00 except the test speed. The test specimen is clamped between two concentric rings whose inner diameter defines the circular area under test. A penetration assembly, the top of which is a smooth, spherical steel ball, is arranged perpendicular to and centered under the rings holding the test specimen. The penetration assembly is raised at 6 inches per minute such that the steel ball contacts and eventually penetrates the test specimen to the point of specimen rupture. The maximum force applied by the penetration assembly at the instant of specimen rupture is reported as the burst strength in grams force (gf) of the specimen.

The penetration assembly consists of a spherical penetration member which is a stainless steel ball with a diameter of 0.625±0.002 inches (15.88±0.05 mm) finished spherical to 0.00004 inches (0.001 mm). The spherical penetration member is permanently affixed to the end of a 0.375±0.010 inch (9.525±0.254 mm) solid steel rod. A 2000 gram load cell is used and 50 percent of the load range i.e. 0-1000 g is selected. The distance of travel of the probe is such that the upper most surface of the spherical ball reaches a distance of 1.375 inches (34.9 mm) above the plane of the sample clamped in the test. A means to secure the test specimen for testing consisting of upper and lower concentric rings of approximately 0.25 inches (6.4 mm) thick aluminum between which the sample is firmly held by pneumatic clamps operated under a filtered air source at 60 psi. The clamping rings are 3.50±0.01 inches (88.9±0.3 mm) in internal diameter and approximately 6.5 inches (165 mm) in outside diameter. The clamping surfaces of the clamping rings are coated with a commercial grade of neoprene approximately 0.0625 inches (1.6 mm) thick having a Shore hardness of 70-85 (A scale). The neoprene needs not cover the entire surface of the clamping ring but is coincident with the inner diameter, thus having an inner diameter of 3.50±0.01 inches (88.9±0.3 mm) and is 0.5 inches (12.7 mm) wide, thus having an external diameter of 4.5±0.01 inches (114±0.3 mm). For each test a total of 3 sheets of product are combined.

The sheets are stacked on top of one another in a manner such that the machine direction of the sheets is aligned. Where samples comprise multiple plies, the plies are not separated for testing. In each instance the test sample comprises 3 sheets of product. For example, if the product is a 2-ply tissue product, 3 sheets of product, totaling 6 plies are tested. If the product is a single ply tissue product, then 3 sheets of product totaling 3 plies are tested.

Samples are conditioned under TAPPI conditions for a minimum of four hours and cut into 127×127±5 mm squares. For wet burst measurement, after conditioning the samples were wetted for testing with 0.5 mL of deionized water dispensed with an automated pipette. The wet sample is tested immediately after insulting.

The peak load (gf) and energy to peak (g-cm) are recorded and the process repeated for all remaining specimens. A minimum of five specimens are tested per sample and the peak load average of five tests is reported.

Tear

Tear testing was carried out in accordance with TAPPI test method T-414 "Internal Tearing Resistance of Paper (Elmendorf-type method)" using a falling pendulum instrument such as Lorentzen & Wettre Model SE 009. Tear strength is directional, and MD and CD tear are measured independently.

More particularly, a rectangular test specimen of the sample to be tested is cut out of the tissue product or tissue base sheet such that the test specimen measures 63±0.15 mm (2.5±0.006 inches) in the direction to be tested (such as the MD or CD direction) and between 73 and 114 mm (2.9 and 4.6 inches) in the other direction. The specimen edges must be cut parallel and perpendicular to the testing direction (not skewed). Any suitable cutting device, capable of the prescribed precision and accuracy, can be used. The test specimen should be taken from areas of the sample that are free of folds, wrinkles, crimp lines, perforations or any other distortions that would render the test specimen abnormal from the rest of the material.

The number of plies or sheets to test is determined based on the number of plies or sheets required for the test results to fall between 20 to 80 percent on the linear range scale of the tear tester and more preferably between 20 to 60 percent of the linear range scale of the tear tester. The sample preferably should be cut no closer than 6 mm (0.25 inch) from the edge of the material from which the specimens will be cut. When testing requires more than one sheet or ply the sheets are placed facing in the same direction.

The test specimen is then placed between the clamps of the falling pendulum apparatus with the edge of the specimen aligned with the front edge of the clamp. The clamps are closed and a 20-millimeter slit is cut into the leading edge of the specimen usually by a cutting knife attached to the instrument. For example, on the Lorentzen & Wettre Model SE 009 the slit is created by pushing down on the cutting knife lever until it reaches its stop. The slit should be clean with no tears or nicks as this slit will serve to start the tear during the subsequent test.

The pendulum is released and the tear value, which is the force required to completely tear the test specimen, is recorded. The test is repeated a total of ten times for each sample and the average of the ten readings reported as the tear strength. Tear strength is reported in units of grams of force (gf). The average tear value is the tear strength for the direction (MD or CD) tested. The "geometric mean tear strength" is the square root of the product of the average MD tear strength and the average CD tear strength. The Lorentzen & Wettre Model SE 009 has a setting for the number of plies tested. Some testers may need to have the reported tear strength multiplied by a factor to give a per ply tear strength. For base sheets intended to be multiple ply products, the tear results are reported as the tear of the multiple ply product and not the single ply base sheet. This is done by multiplying the single ply base sheet tear value by the number of plies in the finished product. Similarly, multiple ply finished product data for tear is presented as the tear strength for the finished product sheet and not the individual plies. A variety of means can be used to calculate but in general will be done by inputting the number of sheets to be tested rather than the number of plies to be tested into the measuring device. For example, two sheets would be two 1-ply sheets for 1-ply product and two 2-ply sheets (4-plies) for 2-ply products.

Tensile

Tensile testing is conducted on a tensile testing machine maintaining a constant rate of elongation and the width of each specimen tested is 3 inches. Testing is conducted under TAPPI conditions. Prior to testing samples are conditioned under TAPPI conditions (23±1° C. and 50=2 percent relative humidity) for at least 4 hours and then cutting a 3±0.05 inches (76.2±1.3 mm) wide strip in either the machine direction (MD) or cross-machine direction (CD) orientation using a JDC Precision Sample Cutter (Thwing-Albert Instrument Company, Philadelphia, PA, Model No. JDC 3-10, Serial No. 37333) or equivalent. The instrument used for measuring tensile strengths was an MTS Systems Sintech 11S, Serial No. 6233. The data acquisition software was MTS TestWorks® for Windows Ver. 3.10 (MTS Systems Corp., Research Triangle Park, NC). The load cell was selected from either a 50 Newton or 100 Newton maximum, depending on the strength of the sample being tested, such that the majority of peak load values fall between 10 to 90 percent of the load cell's full-scale value. The gauge length between jaws was 4±0.04 inches (101.6±1 mm) for facial tissue and towels and 2±0.02 inches (50.8±0.5 mm) for bath tissue. The crosshead speed was 10±0.4 inches/min (254±1 mm/min), and the break sensitivity was set at 65 percent. The sample was placed in the jaws of the instrument, centered both vertically and horizontally. The test was then started and ended when the specimen broke. The peak load was recorded as either the "MD tensile strength" or the "CD tensile strength" of the specimen depending on direction of the sample being tested. Ten representative specimens were tested for each product or sheet and the arithmetic average of all individual specimen tests was recorded as the appropriate MD or CD tensile strength having units of grams per three inches (g/3"). Tensile energy absorbed (TEA) and slope are also calculated by the tensile tester. TEA is reported in units of g·cm/cm$^2$ and slope is recorded in units of kilograms (kg). Both TEA and Slope are directionally dependent and thus MD and CD directions are measured independently.

All products were tested in their product forms without separating into individual plies. For example, a 2-ply product was tested as two plies and recorded as such. In the tensile properties of basesheets were measured, the number of plies used varied depending on the intended end use. For example, if the basesheet was intended to be used for 2-ply product, two plies of basesheet were combined and tested.

Surface Smoothness

Surface smoothness was measured using an EMTEC Tissue Softness Analyzer ("TSA") (Emtec Electronic GmbH, Leipzig, Germany). The TSA comprises a rotor with vertical blades which rotate on the tissue sample applying a defined contact pressure. The blades are pressed against the sample with a load of 100 mN and the rotational speed of the blades is two revolutions per second. Contact between the vertical blades and the tissue sample creates vibrations, which are sensed by a vibration sensor. The sensor transmits a signal to a PC for processing and display. The signal is displayed as a frequency spectrum. The frequency spectrum is analyzed by the associated TSA software to determine the amplitude of the frequency peak occurring in the range between 200 to 1000 Hz. This peak is generally referred to as the TS750 value (having units of dB $V^2$ rms) and represents the surface smoothness of the tissue sample. A high amplitude peak correlates to a rougher surface, while a low amplitude peak correlates a smoother surface.

Tissue product samples were prepared by cutting a circular sample having a diameter of 112.8 mm. All samples were allowed to equilibrate at TAPPI conditions for at least 24 hours prior to completing the TSA testing. After conditioning each sample was tested as-is, i.e., multi-ply products were tested without separating the sample into individual plies. The sample is secured, and the measurements are started via the PC. The PC records, processes and stores all of the data according to standard TSA protocol. The reported TS750 value is the average of five replicates, each one with a new sample.

EXAMPLES

Basesheets were made using a through-air dried papermaking process commonly referred to as "uncreped through-air dried" ("UCTAD") and generally described in U.S. Pat. No. 5,607,551, the contents of which are incorporated herein in a manner consistent with the present disclosure. Basesheets with a target bone dry basis weight of about 25 grams per square meter (gsm) were produced. The base sheets were then converted into embossed two-ply tissue products.

Basesheets were prepared using a three-layered headbox to form a web having a first outer layer, also referred to as the fabric or fabric contacting layer, a middle layer, and a second outer layer, also referred to the air contacting or air layer, Various wood pulp fibers including, southern softwood kraft pulp (SSWK), eucalyptus hardwood kraft pulp (EHWK) and northern softwood kraft pulp (NSWK), were used to form the various furnish layers as detailed in Table 3, below. In certain instances, a debonder was added to the fabric contacting layer and/or a dry strength resin was added to the middle layer as detailed in Table 3, below.

Each furnish was diluted to approximately 0.2 percent consistency and delivered to a layered headbox and deposited on a Voith Fabrics TissueForm V forming fabric (commercially available from Voith Fabrics, Appleton, WI). The wet web was vacuum dewatered to approximately 25 percent consistency and then subjected to rush transfer when transferred to the transfer fabric. The transfer fabric was the fabric described as "Fred" in U.S. Pat. No. 7,611,607 (commercially available from Voith Fabrics, Appleton, WI). The rush transfer rate was 28 percent. The web was then transferred to a Tissue Max EX through-air drying fabric (commercially available from Voith Fabrics, Appleton, WI). The web was dried with a through-air-dryer resulting in dried tissue web.

The dried tissue web was fed to a gravure printing line, similar to that shown in FIG. 3, traveling at about 1,000 feet per minute where a latex polymer was printed onto the surface of the sheet. The binder composition was varied for each of the sample codes as indicated in Table 4, below. Each of the binders are commercially available from Wacker Polymers, LP (Allentown, PA).

TABLE 4

| Sample | Binder | % Solids |
|---|---|---|
| Inventive 1 | Vinnapas ™ EZ123 | 30 |
| Inventive 2 | Vinnapas ™ EP1133 | 15 |
| Inventive 3 | Vinnapas ™ EP1133 | 30 |
| Inventive 4 | Vinnapas ™ EP1133 | 30 |
| Inventive 5 | Vinnapas ™ EP1133 | 30 |

The pH of the latex-based binder was adjusted using NaOH to a pH of approximately 6.0 and allowed to mix for approximately 5 to 30 minutes prior to use in the gravure printing operation. The viscosity of the latex-based binder was in range from 30 to 60 cps when measured at room temperature using a viscometer (Brookfield™ Synchrolectric viscometer Model RVT, Brookfield Engineering Laboratories Inc. Stoughton, MA) with a #1 spindle operating at 20 rpm.

The first side of the dried web was printed with a binding composition using direct rotogravure printing in a pattern as shown in FIG. 5. The pattern comprises three elongated hexagons having a length of about 0.02 inch (0.51 mm) and a width of about 0.006 inch (0.15 mm). After printing, the sheet was pressed against and doctored off a rotating drum, which had a surface temperature of approximately 126° C.

The print creped tissue web was subjected to further converting to produce a two-ply tissue product. Individual tissue webs were embossed and plied using an embossing-laminating device, such as those described in U.S. Pat. No. 3,867,225. The individual plies were arranged such that the surface printed with the binder composition formed the two outer surface of the two-ply tissue product.

After embossing and lamination the two-ply tissue product was treated with a softening composition. The contents of the softening composition are provided in Table 5, below.

TABLE 3

| Sample | First Outer Layer (wt %) | Middle Layer (wt %) | Second Outer Layer (wt %) | Chemical Add-On (kg/MT) |
|---|---|---|---|---|
| Inventive 1-4 | EHWK (30%) | NSWK (40%) | EHWK (30%) | ProSoft ® TQ-1003 (1.5)<br>FennoBond ® 3300 (0.5) |
| Inventive 5 | SSWK | SSWK | SSWK | ProSoft ® TQ-1003 (1.5) |

TABLE 5

| | Softening Composition No. 1 | Softening Composition No. 2 |
|---|---|---|
| Silicone (wt %) | 22.5 | 2 |
| Glycerin (wt %) | — | 6 |
| Nonionic Surfactant (wt %) | 7.5 | 5 |
| PEG-1,000 (wt %) | — | 7 |
| Water (wt %) | 70 | 80 |

The softening compositions were applied by offset gravure printing. The add-on levels where controlled by changing the gravure roll cell volume (measured as BCM—billion cubic microns per square inch), as described in Table 6, below.

TABLE 6

| Sample | Softening Composition | Gravure Roll Cell Volume |
|---|---|---|
| Inventive 1 | 1 | 6 BCM |
| Inventive 2 | 1 | 4 BCM |
| Inventive 3 | 2 | 6 BCM |

The print creped tissue multi-ply web was wound onto a core and converted into a multi-ply rolled tissue product, which was subject to further physical testing as summarized in Tables 7 and 8, below.

TABLE 7

| Sample | Basis Weight (gsm) | Caliper (μm) | Sheet Bulk (cc/g) | GMT (g/3") | Slough (mg) | GM Slope (kg) | Stiffness Index | TS750 |
|---|---|---|---|---|---|---|---|---|
| Inventive 1 | 54.6 | 454 | 9.1 | 1255 | 0.6 | 8.13 | 6.5 | 28.3 |
| Inventive 2 | 53.8 | 445 | 8.3 | 1250 | 0.3 | 8.03 | 6.4 | 31.3 |
| Inventive 3 | 57.4 | 508 | 8.9 | 1631 | 1.18 | 8.50 | 5.2 | 20.8 |
| Inventive 4 | 48.7 | 541 | 11.1 | 956 | 1.48 | 4.91 | 5.1 | 25.6 |
| Inventive 5 | 54.6 | 678 | 12.4 | 1178 | 1.18 | 5.07 | 4.3 | 22.4 |

TABLE 8

| Sample | GM TEA (g·cm/cm$^2$) | Burst (gf) | GM Tear (gf) | Tear Index | TEA Index | Burst Index | Durability Index |
|---|---|---|---|---|---|---|---|
| Inventive 1 | 17.2 | 897 | 13.79 | 1.10 | 1.37 | 7.15 | 9.62 |
| Inventive 2 | 15.9 | 1003 | 16.11 | 1.86 | 1.27 | 8.02 | 11.16 |
| Inventive 3 | 27.4 | 1607 | 23.24 | 1.42 | 1.68 | 9.85 | 12.96 |
| Inventive 4 | 14.5 | 951 | 15.80 | 1.65 | 1.52 | 9.94 | 13.12 |
| Inventive 5 | 18.9 | 1328 | 28.88 | 2.45 | 1.61 | 11.28 | 15.34 |

EMBODIMENTS

First embodiment: A creped, multi-ply tissue product comprising a first and a second tissue ply, the product having a GMT from about 800 to about 1,700 g/3" and a Slough from about 0.25 to about 2.00 mg.

Second embodiment: The product of the first embodiment having a Durability Index from about 10.0 to about 20.0.

Third embodiment: The product of embodiments 1 or 2 having a first outer surface and a non-crosslinked latex polymer disposed thereon.

Fourth embodiment: The product of any one of embodiments 1 through 3 comprising a creping composition consisting essentially of a non-crosslinked vinyl acetate-ethylene polymer and optionally an anti-blocking agent disposed on the first or the second tissue ply. In certain embodiments the creping composition may comprise a polysaccharide or a surfactant.

Fifth embodiment: The product of any one of embodiments 1 through 4 having a TS750 value less than 40.0.

Sixth embodiment: The product of any one of embodiments 1 through 5 having a burst index greater than about 8.0.

Seventh embodiment: The product of any one of embodiments 1 through 6 having a dry burst greater than about 1,000.

Eighth embodiment: The product of any one of embodiments 1 through 7 having a Stiffness Index from about 4.0 to about 10.0.

Ninth embodiment: The product of any one of embodiments 1 through 8 having a TEA Index greater than about 1.50.

Tenth embodiment: The product of any one of embodiments 1 through 9 wherein the first and the second creped tissue plies are through-air dried.

Eleventh embodiment: The product of any one of embodiments 1 through 10 comprising a softener selected from the group consisting of a polyhydroxy compound having a molecular weight of at least about 1,000 g/mol, a diamidoamine quaternary compound, an ester quaternary compound, an alkoxy alkyl quaternary compound, a benzyl quaternary compound, an alkyl quaternary compound, an imidazolinium quaternary compound, a polysiloxane, glycerin, and combinations thereof disposed on the first or the second outer surfaces.

Twelfth embodiment: The product of any one of embodiments 1 through 11 further comprising a plurality of embossments disposed on the first or the second tissue ply.

Thirteenth embodiment: The product of any one of the embodiments 1 through 12 further comprising a plurality of perforations disposed on the first and second tissue plies and wherein the product is a spirally wound bath tissue roll comprising the first and second tissue plies spirally wound around a core.

Fourteenth embodiment: The product of any one of the embodiments 1 through 13 having a basis weight from about 45 to about 60 grams per square meter (gsm).

Fifteenth embodiment: The product of any one of the embodiments 1 through 14 having a Durability Index from about 10.0 to about 20.0.

What is claimed is:

1. A creped, multi-ply tissue product comprising a first creped through-air dried tissue ply and a second creped through-air dried tissue ply, each of the first and second creped through-air dried tissue plies having a first outer surface, wherein at least one of the first outer surfaces comprises a plurality of embossments disposed thereon, the creped, multi-ply tissue product having a geometric mean tensile strength (GMT) from 900 to 1,500 g/3", a Stiffness Index from 4.0 to 8.0 and a TS750 value from about 15.0 to about 40.0.

2. The creped, multi-ply tissue product of claim 1 having a burst index greater than about 8.0.

3. The creped, multi-ply tissue product of claim 1 having a dry burst greater than about 1,000 gf.

4. The creped, multi-ply tissue product of claim 1 having a Slough from 0.25 to about 1.50 mg.

5. The creped, multi-ply tissue product of claim 1 having a basis weight from about 45 to about 60 grams per square meter (gsm).

6. The creped, multi-ply tissue product of claim 1 having a geometric mean slope from about 6.5 to about 8.5 kg.

7. The creped, multi-ply tissue product of claim 1 having a TEA Index from about 1.50 to about 2.25.

8. The creped, multi-ply tissue product of claim 1 having a Durability Index from 10.0 to 20.0.

9. The creped, multi-ply tissue product of claim 1 wherein each of the first and second creped tissue plies comprise fibers consisting essentially of wood pulp fibers.

10. The creped, multi-ply tissue product of claim 9 wherein the wood pulp fibers are softwood kraft pulp fibers, hardwood kraft pulp fibers, or a combination thereof.

11. The creped, multi-ply tissue product of claim 1 further comprising a non-crosslinked latex polymer disposed on at least one of the first outer surfaces.

12. The creped, multi-ply tissue product of claim 11 wherein the non-crosslinked latex polymer is a vinyl acetate-ethylene polymer.

13. The creped, multi-ply tissue product of claim 12 wherein the vinyl acetate-ethylene polymer is carboxylated.

* * * * *